United States Patent
Schneider et al.

(10) Patent No.: US 7,344,727 B2
(45) Date of Patent: *Mar. 18, 2008

(54) PROCESS FOR CLEANING BOVINE TEATS

(75) Inventors: David J. Schneider, Union, KY (US); Charles A. Schneider, Villa Hills, KY (US)

(73) Assignee: H&S Chemical Company, Inc., Covington, KY (US)

( * ) Notice: Subject to any disclaimer, the term of this patent is extended or adjusted under 35 U.S.C. 154(b) by 782 days.

This patent is subject to a terminal disclaimer.

(21) Appl. No.: 10/732,640

(22) Filed: Dec. 10, 2003

(65) Prior Publication Data

US 2005/0058615 A1    Mar. 17, 2005

Related U.S. Application Data

(60) Provisional application No. 60/434,046, filed on Dec. 18, 2002.

(51) Int. Cl.
*A01N 25/02* (2006.01)
*A01N 43/68* (2006.01)

(52) U.S. Cl. .............. 424/405; 424/406; 424/438; 514/245

(58) Field of Classification Search .............. None
See application file for complete search history.

(56) References Cited

U.S. PATENT DOCUMENTS

2005/0069623 A1\* 3/2005 Schneider et al. .......... 426/642

\* cited by examiner

*Primary Examiner*—Neil S. Levy
(74) *Attorney, Agent, or Firm*—Richard M. Klein; Fay Sharpe LLP

(57) ABSTRACT

Animals have been domesticated and kept as a source of milk for tens of thousands of years, When humans keep animals for their ability to produce milk, the animals are usually kept in confined spaces. As a result of this confinement the animals are exposed to high levels of urine and fecal matter which originated with the animals which are being kept. This exposure contaminates the animal and in particular the udder and teats of the animal, with bacteria. In the milking process this bacteria can further contaminate the milk which is destine for human consumption. The bacteria can further cause mastitis in the bovine. The above set forth problems are eliminated in the subject invention wherein the udder and teat areas of the bovine are sanitized with a solution of trichloromelamine.

20 Claims, No Drawings

PROCESS FOR CLEANING BOVINE TEATS

RELATED APPLICATION

This application claims priority of Provisional Application Ser. No. 60/434,046 filed Dec. 18, 2002.

BACKGROUND OF THE INVENTION

Bovines and in particular cows have been milked for thousands of years. Because the udder and teats of a cow are located on its underside they are easily contaminated with bacteria. In the milking process this bacteria can easily contaminate the resulting milk. In addition this bacteria can spread to the mammary tract of the cows utter causing infections which are referred to as mastitis. These infections can severely restrict the amount of milk produced by the cow, and hence the economics of the dairy in question.

In the past efforts have been made to sanitize the teats and udder areas of a bovine prior to the milking process. Past attempts to sanitize the udder and teats consisted of washing with soap, and water and washing with solutions of iodine based compounds.

These prior art attempts to sanitize the udder and teats of a bovine have proved to be ineffective and/or troublesome.

This application relates to sanitizing the udder and teats of an animal prior to the milking process. While this application primarily refers to sanitizing the udder and teats of a bovine, it is understood by one skilled in the art, that the process of this invention is applicable to any milk giving animal.

PRIOR ART

In the past the milking of bovines has often been effected on unsanitary udders and teats. Often in the past the udders and teats were only washed if washed at all, with un-sanitized water.

Early in the twentieth century to a limited degree the udders and teats of bovines were washed with crude soap prior to the milking process. While washing with soap helped, to a limited degree, the under and teats of the bovine were not sanitized by this procedure.

In the past few decades it has become common to sanitize the udders and teats of a bovine prior to and after the milking process. The most common sanitizing agents used are solutions of iodine or iodine compounds. While these iodine based solutions are effective in killing bacteria they have drawn back such as;

1. Iodine based compounds are hard on the tissue of the udder and teats.
2. Iodine based sanitizing solutions tend to stain the udder and teats and the hands and clothing of the operator.
3. Iodine based sanitizing solutions must be shipped in liquid form. This shipping of water substantially increases the shipping cost.
4. Iodine based sanitizing solutions are expensive.

While the use of Cl+ based solutions to clean the udder and teat areas of bovine animals may have taken place in countries foreign to the United States the applicant is not aware of printed references to these usages.

This invention is concerned with the use of solutions of trichloromelamine (TCM) for sanitizing the udder and teat areas of animals prior to milking. The applicant is further not aware of any disclosure of the use of TCM for this purpose.

BRIEF DESCRIPTIONS OF THE INVENTION

The udder and teat area of bovines are often contaminated with bacteria. During the milking process this bacterial can be transferred to the milk with severe consequences. Further the bacteria can cause the infection of the teats, these infections are referred to as mastitis. These infections can detrimentally affect milk production and the overall health of the animal.

In accordance wit this invention the udder and teat areas of an animal may be sanitized and infections of the teats eliminated by washing the udder and teat areas with a solution of trichloromelamine (TCM).

In accordance with this invention the udder and teat washing is effected with a solution which contains an effective amount of TCM.

The solutions of TCM for use in this invention may further incorporate additives which aid in the sanitizing process or aid in enhancing the health and well being of the animal which is being milked.

OBJECTS OF THE INVENTION

The primary object of this invention is a process for sanitizing the udder and teat areas of an animal.

Still another object of this invention is a process for sanitizing the udder and teat areas of an animal using a pre dip. A further object of this invention is a process for sanitizing the udder and teat areas of an animal using a post dip.

Another object of this invention is a process for sanitizing the udder and teat areas of an animal using both pre and post dips.

Another object of this invention is a process for sanitizing the udder and teat areas of an animal with trichloromelamine wherein dry reagents are utilized.

DESCRIPTION OF THE PREFERRED EMBODIMENT

Animals have been domesticated by man and kept for their milk production for thousands of years. In order that the animals might be controlled and restrained they are most often kept in a confined space i.e. a herd of dairy cows which are kept in a dairy barn. In fact the process of this invention is most often utilized with dairy cows which are kept in a dairy barn.

Because domesticated animals are kept in a confined space, as is discussed above, they are often kept in unsanitary conditions. These unsanitized conditions result from the fact that the under side areas of the animals come into contact with urine a fecal matter. This urine and fecal matter naturally is contaminated with a wide range of bacteria such as *E Coli*. This bacteria can contaminate the milk, if the udder and teat areas of the cow are not sanitized prior to the milking process.

In this application references will often be made to sanitizing the udder and teat areas of cows. It is understood by one skilled in the art that the process of this invention is also applicable to other animals such as goats. In fact the process of this invention is applicable to any animal which gives milk.

As a broad overview this invention is concerned with a process for sanitizing the udder and teat areas of an animal using trichloromelamine, hereinafter TCM. A very common sanitizing agent is bleach which kills a wide spectrum of bacteria. Solutions of sodium hypochlorite are referred to as bleach. While bleach is a very effective biocide its action is very harsh on living tissue. As such solutions of bleach are not suitable as a biocide for dairy animals. That is if a solution of bleach were applied to the udder and teat areas of a cow the bacteria would be killed however, the tender tissue of these areas would be adversely affected. In fact if bleach were applied to the udder and teat areas of a cow, one would have a very unhappy cow.

The active agent in bleach is the Cl+ ion which is capable of killing a wide spectrum of bacteria.

This invention relates to the use of trichloromelamine as an active agent for sanitizing the udder and teat areas of cows. Like bleach TCM produces the Cl+ ion which is capable of killing a wide spectrum of bacteria. The Cl+ ion produced by TCM is latent and hence its effect on living tissue is not as harsh as Cl+ ion produced by solutions of sodium hypochlorite. Solutions of sodium hypochlorite are generally not suitable for use on living tissue. When soft living tissue is treated in accordance with this invention, the troublesome bacteria are killed in a matter of seconds and the treated living tissue is not adversely affected.

TCM has been used as a biocide for sanitizing objects such as kitchen utensils however, it has not been used to sanitize the udder and teat areas of dairy animals.

The process of this invention is effected by spraying the udder and teat areas of a bovine with a solution of TCM.

The process may be further effected by dipping the udder and teat areas in a solution of TCM.

A broad range for the concentration of TCM used in the solution of this invention is from about 50 to about 500 ppm, with a more preferred range being from about 100 to about 300 ppm, a most preferred range is from about 150 to about 250 ppm. A most preferred concentration for TCM in solution for use in this invention is 200 ppm. All of the above specified concentrations are in weight percent.

The TCM solutions for use in this invention may further include other additives such as coloring agents, wetting agents, healing agents, dyes and softeners in order that the bovine teat might be kept healthy and in optimum condition for milk production. The most important additives for use in accordance with this invention, are wetting agents. Wetting agents allow udder and teat areas to wet out. This wetting out allows the TCM to come into contact with the target bacteria.

As to three types of wetting agents, cationic, anionic and nonionic, for use in this invention anionic wetting agents are most preferred, followed by non anionic wetting agents with cationic wetting agents being least preferred.

Examples of suitable wetting agents which are useful in accordance with this invention are: Avanel S-74 and Dodecylbenesulfonic acid (DDBSA).

The most preferred wetting agent for use in this invention is an anionic wetting agent sold under the trademark Avanel S-74 by the BASF Chemical Co. of Mt. Olive, N.J. The applicant believes that Avanel S-74 is Ethoxylated ROH suffonate, where R is $CH_3$, $CH_3 CH_2$ or $CH_2 CH_2$.

An effective amount of the desired wetting agent is used. Solutions containing from about 0.05 to about 2 weight percent of a wetting agent have been found to be effective in accordance with this invention.

Further the performance of TCM solutions in biocide formulations for use in this invention may be further enhanced by additives such phosphates i.e. disodium phosphate, buffering agents etc.

While the TCM is usually applied as an aqueous solution other solvents may be used.

TCM is highly soluble in water therefore solutions in accordance with this invention can be easily compounded. Because these solutions can be easily compounded the TCM can be shipped in dry powder form in pre measured packets. The shipment in dry powder form results in substantial savings in shipping cost as compared to the prior art iodine solutions which must be shipped as solutions.

The process of this invention may be used prior to the milking process, pre dip, after the milking process, post dip, and both as a pre dip and post dip.

The process of this invention effectively kills all bacteria as may be on the udder and teat areas of a bovine in less than one minute.

The process of this invention is further advantageous in that it leaves residual TCM on the udder and teat areas which inhibits future bacterial contamination.

What is claimed is:

1. A process for sanitizing the udder and teat areas of an animal which comprises applying an effective amount of trichloromelamine to the udder and teat areas of said animal.

2. The process of claim 1 wherein the trichloromelamine is applied as a solution.

3. The process of claim 2 wherein the solution is an aqueous solution.

4. The process of claim 2 wherein the concentration of trichioromelamine, in said solution, is from about 50 to about 500 ppm.

5. The process of claim 3 wherein the concentration of trichloromelamine, in said solution, is from about 50 to about 500 ppm.

6. The process of claim 2 wherein the concentration of trichloromelamine, in said solution, is from about 100 to about 300 ppm.

7. The process of claim 3 wherein the concentration of trichloromelamine, in said solution, is from about 100 to 300 ppm.

8. The process of claim 2 wherein the concentration of trichloromelamine, in said solution, is from about 150 to about 250 ppm.

9. The process of claim 3 wherein the concentration of trichloromelamine, in said solution, is from about 150 to about 250 ppm.

10. The process of claim 2 wherein the concentration of trichloromelamine, in said solution, about 200 ppm.

11. The process of claim 3 wherein the concentration of trichloromelamine is about 200 ppm.

12. The process of claim 5 wherein the solution of trichloromelamine is applied pre milking.

13. The process of claim 5 wherein the solution of trichloromelamine is applied post milking.

14. The process of claim 5 when the solution of trichloromelamine is applied both pre milking and post milking.

15. The process of claim 9 wherein the solution of trichloromelamine is applied pre milking.

16. The process of claim 9 wherein the solution of trichloromelamine is applied post milking.

17. The process of claim 9 when the solution of trichloromelamine us applied both pre milking and post milking.

18. The process of claim 15 wherein the solution of trichloromelamine further incorporate an effective amount of a wetting agent.

19. The process of claim 16 wherein the solution of trichloromelamine further incorporate an effective amount of a wetting agent.

20. The process of claim 17 wherein the solution of trichloromelamine further incorporate an effective amount of a wetting agent.

* * * * *